United States Patent [19]

Gustafsson

[11] Patent Number: 5,320,618
[45] Date of Patent: Jun. 14, 1994

[54] DEVICE FOR TREATMENT OF UNDESIRED SKIN DISFIGUREMENTS

[76] Inventor: Morgan Gustafsson, Mellangatan 23, S-413 01 Göteborg, Sweden

[21] Appl. No.: 934,516

[22] PCT Filed: Apr. 9, 1991

[86] PCT No.: PCT/SE91/00260
§ 371 Date: Oct. 7, 1992
§ 102(e) Date: Oct. 7, 1992

[87] PCT Pub. No.: WO91/15264
PCT Pub. Date: Oct. 17, 1991

[30] Foreign Application Priority Data

Apr. 9, 1990 [SE] Sweden ............................ 9001298-0

[51] Int. Cl.⁵ .............................................. A61B 17/36
[52] U.S. Cl. ............................................ 606/9; 606/11; 606/3; 606/16
[58] Field of Search ................. 606/4, 14, 15, 16, 17, 606/18, 27, 28, 32, 34, 41, 10, 11, 2, 3, 9; 128/395, 396, 397, 398

[56] References Cited

U.S. PATENT DOCUMENTS

| | | |
|---|---|---|
| 3,327,712 | 6/1967 | Kaufmann et al. |
| 3,693,623 | 9/1972 | Harte et al. ............................. 606/9 |
| 4,233,493 | 11/1980 | Nath ..................................... 606/16 |
| 4,747,660 | 5/1988 | Nishioka et al. ..................... 606/14 |
| 4,832,024 | 5/1989 | Boussignac et al. ................. 606/15 |
| 4,860,172 | 8/1989 | Schlager et al. ..................... 606/17 |

FOREIGN PATENT DOCUMENTS 2044908 10/1980 United Kingdom ................ 128/397

OTHER PUBLICATIONS

International Publication No. WO 89/00871 Apparatus for Irradiating by Polarised Light 22 Jul. 1988, Katona et al.

Primary Examiner—Stephen C. Pellegrino
Assistant Examiner—Sonya Harris
Attorney, Agent, or Firm—Eugene E. Renz, Jr.

[57] ABSTRACT

The present invention relates to a device for treating of superficial afflictions of the type telangiectasis by means of a directed light beam. The device can be produced at a very low cost compared with known devices due to the fact that a source of light (2) that produces non-coherent light is used, that means due to a non-use of laser.

8 Claims, 5 Drawing Sheets

DEVICE FOR TREATMENT OF UNDESIRED SKIN DISFIGUREMENTS

TECHNICAL FIELD

The present invention relates to a device for treating telangiectasis and the like afflictions such as capillary hemangroma (red birthmarks).

PRIOR ART AND PROBLEM

It is known today that telangiectasis can be removed by means of a laser. By directing the laser beam in a prescribed way against the superficial affliction that is to be treated a such aesthetically disturbing affliction can be completely eliminated in that the laser beam burns away the cellular tissue that gives rise to the affliction. On the market today a plurality of different devices are available for carrying out such a treatment mentioned above. One common aspect for all available devices is a high price. This high price depends on the fact that the laser beam devices as such require part components which are very costly. The high price for the device results in its turn in that the availability of the treatment method is relatively low as this gives rise to relatively few devices on the market and that each treatment will be relatively expensive.

THE SOLUTION AND ADVANTAGES

The object of the present invention is to bring about a device that eliminates the above mentioned problems and which accordingly results in a high accessibility to the above described treatment method.

Said object has surprisingly been obtained by means of a device according to what has been stated in claim 1.

DESCRIPTION OF THE FIGURES

The invention will be further described in the following with reference to the attached drawings in which:

FIG. 1 shows the principle construction of a device according to the invention. Thus, a spherical reflector 1 is shown, within which a lamp 2 is arranged. The lamp is of a high efficient type, suitably a so-called arc-lamp. The reflector has a reflecting inner surface 10 and an opening 11 for the outgoing rays. The outgoing rays converge towards a fixed point where a first lens 3 is arranged. The lens 3 is of a convex type that converts the conveying rays to parallel light. The parallel beam of rays is thereafter directed into a device 6 which by filtration brings about a desired area of wave lengths. Such a device can for example be a monochromator 6 or a filter 6. The ray beam coming out of the device 6 is fed into a fibre optical cable 4. Via fibre optical cable 4 the rays are conducted forward to a second lens 5 which is arranged at the outer end of the fibre optical cable 4. The end 50 of this second lens 5 is intended to be directed towards the superficial part of a human body that is to be treated.

Figure 1:
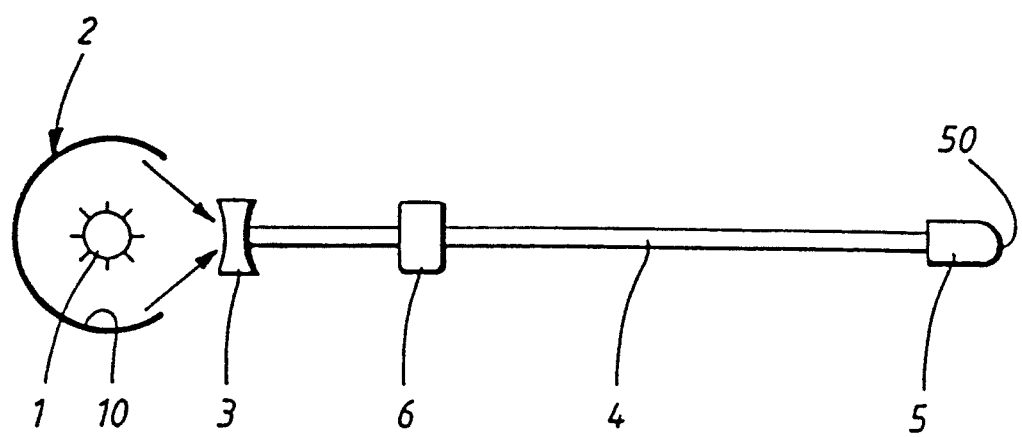
FIG. 1 shows principally the construction of a device according to the invention.

To obtain the best possible result the light source is in the preferred embodiment an arc-lamp which has an effect peak of about 585 nm. This wavelength will vary over an interval of + or −10% , or preferably + or −5%, about the peak wavelength in the band. Preferably a converging reflector 1 having an inner surface 10 which maximizes the reflection of rays having a wave length about 585 nm is used. Further in the preferred embodiment the second lens 5 shall be so arranged that the beam of rays and the exit from the lens has a diameter of 0.5-5 mm preferably 3 mm. If, however, effect at the desired area of wave length is comparatively low it is preferred to further minimize the diameter of the ray beam coming from the second lens 5.

The light is in its preferred embodiment consisting of pulses having a duration of 450 microseconds (also continuous light can be used). The pulses can either be produced directly in the lamp or at a later stage along the way of the beams by means of a mechanical or electronic closure. The length of the pulse can, in its extreme case, be so low as 15 microseconds $(1.5 \times 10^{-10})$ however, suitably in the interval 50 microseconds to 0.5 seconds and preferably within the area of 0.1-100 milliseconds, where most preferred is a pulse of 0.1 to about 2 milliseconds or up to about 10 milliseconds. The frequency of the pulses can vary within wide rang but should preferably be within the interval 1-1000 hertz.

Pulses shorter than 15 microseconds may give rise to vascular damages and bleeding, whereas for long pulses, according to the principle of "completely fried" gives (depending on the thickness of the vasculars) more burn injuries, burn wounds, scars, more pain, etc.

It is possible by means of the above described arrangement to successfully treat telangiectasis and other not desirable superficial afflictions such as birthmarks at a reasonable cost. The rays made in the above way do burn away these undesirable afflictions by means of a device according to the invention by using a so-called "conventional" light of source that means not source for laser rays.

Figure 2:
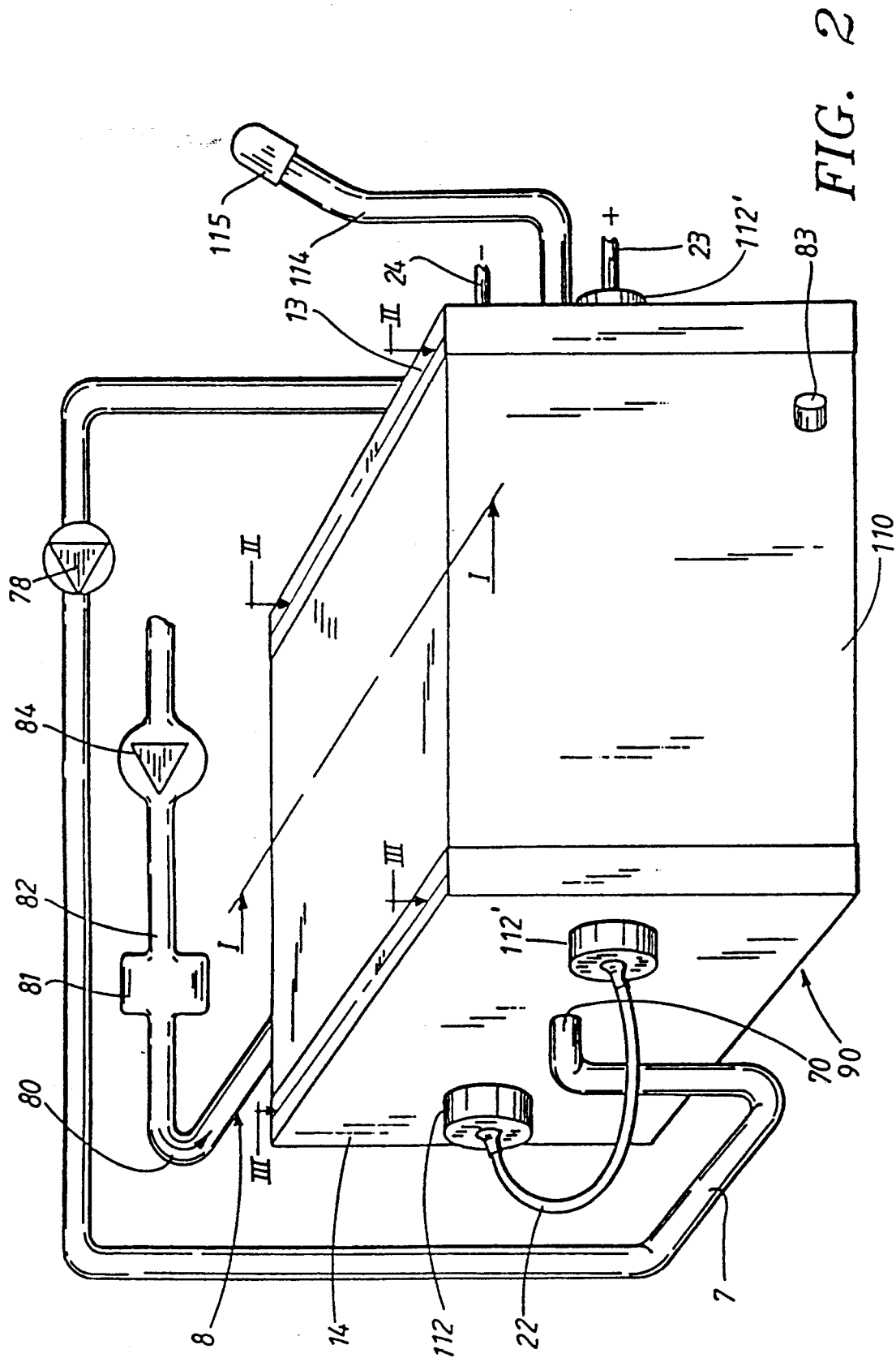
FIG. 2 shows a preferred embodiment in a perspective view.

FIG. 2 shows a preferred embodiment of a device according to the invention. This includes a cover 1, consisting of two end covers 13, 14 at each end and a middle part 11 which carries a reflecting bowed surface 10, preferably shaped elliptically. The middle part is preferably made in a material which is sold under the trade mark "Spectralon", substantially consisting of titanium dioxide (ca 95%) and plastics. The end covers 13, 14 are preferably made from white PTFE ("Teflon"). In longitudinal direction, arranged, in parallel the cover 1 is penetrated by two pipe shaped xenon gas filled lamps 2. The lamps 2 are connected in series via a lead 22 in one of the end covers 14 and have in the other end +23 respectively −24 connections. A preferred voltage is about 2.000 volts which are obtained by means of suitable condensers. The pulse time is for this device preferably between ½-1 millisecond and the frequency is preferably between 1-2 hertz.

To receive the light emitted from the lamps 2 a middle pipe 71 is arranged having at its one end 70 a hose 7 which is connected to the pressure side of a circulation pump 78, which recirculates a liquid 72 through said pipe 71. Further it is shown that the cover 1 is arranged to have a cooling system 8 consisting of a pump 84 and a deionizing filter 81, a hose 82 and an outlet pipe 83 and an inlet pipe. The flow is preferably about 6 1/min. A fibre optical cable 4 is also arranged which at its one end preferably carries a lens 5 according to what has been described earlier. This arrangement functions thus in principle as the earlier described base model but is due to its construction much more effective.

Figure 3:
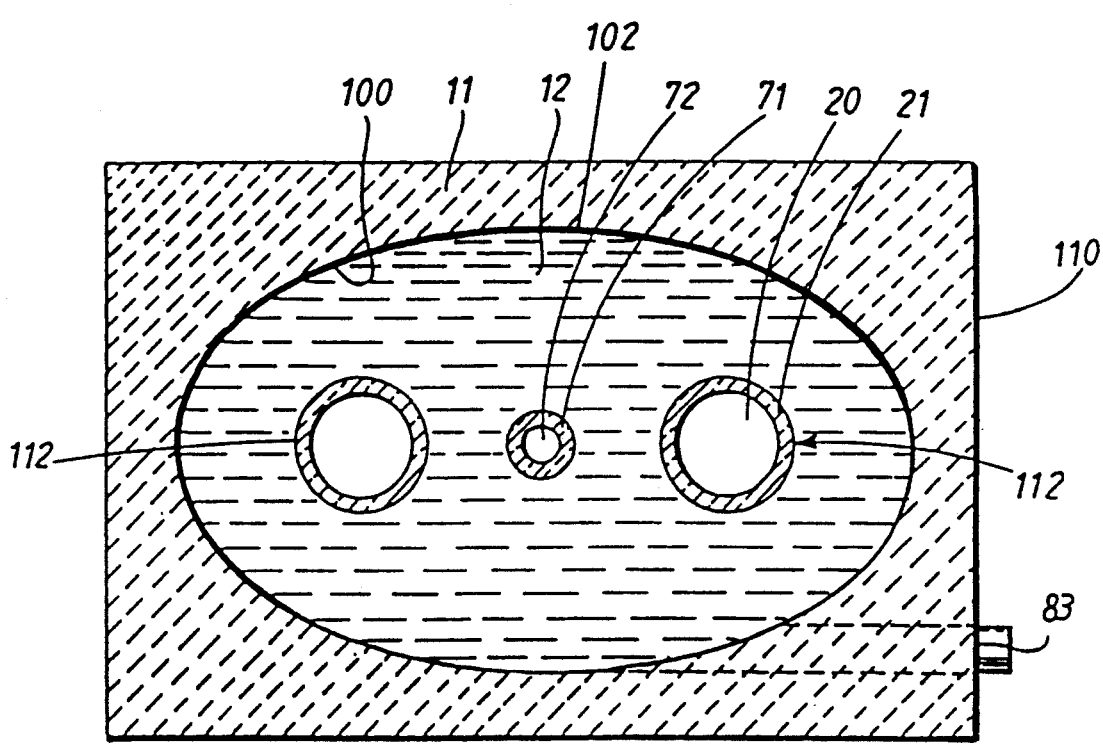
FIG. 3 shows a cross-section along the line I—I in FIG. 2.

FIG. 3 shows a cross-section through the middle part 11. The pipe shaped cover 21 of the lamps includes a gas, preferably xenon, in its interior 20. The middle pipe 71 consists suitably of quarts glass and includes a liquid which preferably changes blue-green light to yellow light. Such a compound is marketed with the name "Rhodamin", preferably Rhodamin 6G, changing a comparatively large amount of the light emitted from the lamps preferably the blue-green spectrum to the desired wave length. A suitable concentration is about 2 g Rhodamin (solids content)/liter liquid. The liquid base is for example an alcohol or a mixture of alcohols, preferably methanol and/or ethanol. The reflection index for the liquid should differ strongly from the reflection index in the pipe 71. A suitable flow for the liquid is about 4 liter/min. The cooling liquid (deionized water) flows through the cavity 12 in a direction square to the pipes 2, 71. The exit- 83 and inlet connection pieces are located diametrically to each other and in each end.

Figure 4A:
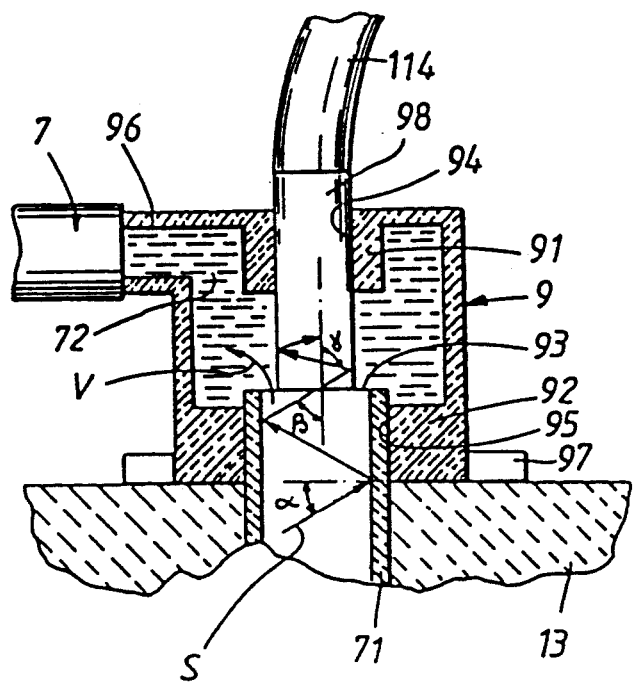
FIG. 4 shows parts of a longitudinal section through the device according to FIG. 2.
Figure 4B:
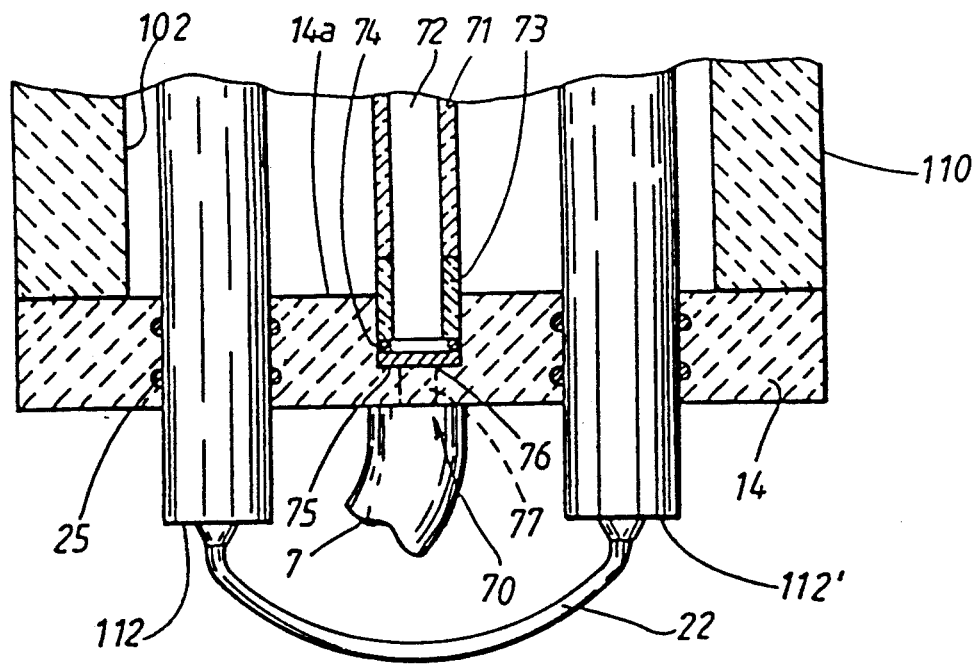

FIG. 4 shows two important parts in a longitudinal section. As also appears from FIG. 2, the inlet 70 for the liquid 72 in the pipe 71 is oblique. This has been made to minimize the reflection losses through the hole 76 and the channel 77 that connects the content in the pipe 72 with the circulation hose 7. Said hole 76 has been arranged in a highly reflecting circular plate 75, for example of stainless steel. Between the plate 75 and the pipe end 73 is for sealing off an O-ring, preferably in white viton arranged. The lower end 73 of the pipe 71 has suitably been made in a white opal glass to get high reflection at this end, whereas other parts of the pipe 71 have been made of transparent quarts glass. The end piece 14 which is made of white teflon and has an added inner high reflecting surface 14a (glue attached metal foil, etc), is in a suitable way for example by gluing, screwing, etc, connected with the middle part 11 (relates also to 13). To seal off the passage of the lamps 2 through the end covers 13 and 14 two O-rings 25 have been arranged at each passage.

At the other end cover the rear end of the fibre optical cable 4 is connected to a glass rod 98 for receiving the light transported through the pipe 71. By means of suitably chosen reflection indexes of the materials used which reflect and transport the rays (s) a preferable reflection angle is obtained for the major part of the rays. This reflection angle ($\alpha$) is in the pipe 71 for example 30° (compared to the normal), which gives an angle of incidence ($\beta$) at the end of the fibre optical cable 4 of for example 60°. A still greater angle ($\Gamma$) of the rays is obtained within the optical coupling rod 98, depending on which reflective index is chosen. Thereafter a small reflection angle is obtained in the same way within the fibre optical cable 4.

The fibre optical cable 4 is secured by means of a clamp within the cavity 94 of a ring shaped part of the coupling part 9. This coupling part 9 can also advantageously be integrated in the end cover 13. This coupling part 9 combines the pipe 71 with the optical coupling rod 98 in such a way that their ends substantially are in one and the same plane. The pipe 71 is also secured by means of a clamp of a ring shaped part 92 of the coupling 9. To make a through flow possible a small slot 93 is arranged between the two parts. The optical coupling rod 98 has preferably a diameter which is 1 mm smaller than the inner diameter of the pipe 71. Via a coupling pipe 96 the coupling 9 is connected to the house 7 for recirculation. The coupling 9 is preferably made in white PTFE Teflon, having also fastening means 97 for fixing by means of screws at the end cover 13.

Figure 5:
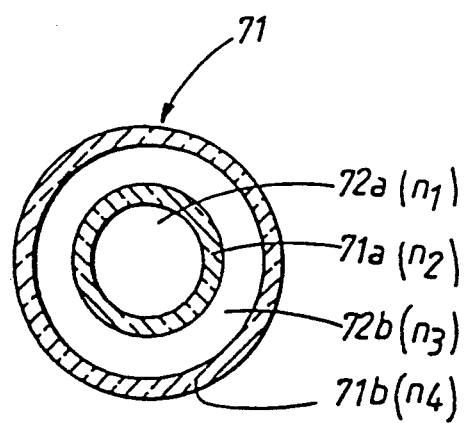
FIG. 5 shows a cross-section through an alternative middle pipe.

FIG. 5 shows an alternative embodiment of the middle pipe 71, and it consists of two coaxial pipes 71a, 71b. In a first embodiment the middle space 72b is filled by air and the inner 72a preferably with Rhodamin. The reflection indexes are such that $n_1 \approx n_2$ which deviates strongly from $n_3$ at the same time as $n_4$ suitably is between the refraction index for water and air. In a second embodiment the outer space 72b is instead filled with a liquid (for example methanol and/or ethanol) containing about 4 g/l of a compound which is sold under the trade mark "Cumarin", suitably Cumarin 156. This compound has the ability to change UV-light to blue-green light which later in the pipe is changed by the Rhodamin according to what has been explained earlier. Then the reflection indexes $n_2 \approx n_3 \approx n_4$ strongly differing from $n_1$. Further all liquids 72 contain a "tripletquencher", which stabilizes surplus energy from exited molecules in some of the said compounds.

The man skilled in the art will realize that the invention is not limited to the above shown, but can be changed within the scope of the following claims. Thus, it is for example possible that in the interior 72 or 72a to mix both "Cumarin" and "Rhodamin". Instead of "Spectralon" highly polished aluminum can for example be used etc.

What is claimed is:

1. A device for the treatment of undesired superficial skin afflictions such as telangiectasis, comprising:
    light transforming means for transforming a first predetermined wavelength band of light to a second predetermined pulsed wavelength band of light;
    a first light source for producing light including said first predetermined wavelength band; and
    guide means for directing said second predetermined pulsed wavelength band to a predetermined location.

2. The device of claim 1 wherein said first and second wavelength bands have a width of up to 10% of the peak wavelength in said band.

3. The device of claim 1 wherein said first and second wavelength bands have a width of up to 5% of the peak wavelength in said band.

4. The device of claim 1 wherein said light transforming means is a light transforming liquid solution.

5. The device of claim 4 wherein said solution comprises a dye solution.

6. The device of claim 1 wherein said light is pulsed from about 0.1 to about 10 milliseconds.

7. The device of claim 1 wherein said light is pulsed from about 0.1 to about 2 milliseconds.

8. The device of claim 6 wherein said light has a pulse frequency ranging from about 1 to about 1,000 hertz.

* * * * *